United States Patent [19]
Nied

[11] 4,449,029
[45] May 15, 1984

[54] ACOUSTIC WAVE SPOT WELDER ADAPTIVE CONTROL

[75] Inventor: Herman A. Nied, Ballston Lake, N.Y.

[73] Assignee: General Electric Company, Schenectady, N.Y.

[21] Appl. No.: 492,845

[22] Filed: May 9, 1983

[51] Int. Cl.³ .............................................. B23K 11/24
[52] U.S. Cl. ................................... 219/117.1; 73/598; 219/109; 219/110
[58] Field of Search ............ 219/108, 109, 110, 117.1; 73/598, 602, 614, 629; 1/9

[56] References Cited

U.S. PATENT DOCUMENTS

| | | | |
|---|---|---|---|
| 3,384,733 | 5/1968 | Burbank et al. | 219/109 |
| 3,726,130 | 4/1973 | Hurlebaus | 73/67.8 |
| 4,007,631 | 2/1977 | Saifi et al. | 73/71.4 |
| 4,099,045 | 7/1978 | Okuda et al. | 219/109 |

FOREIGN PATENT DOCUMENTS 660799  5/1979  U.S.S.R. ............................ 219/108

OTHER PUBLICATIONS

R. J. Mollica, "Adaptive Controls Automate Resistance Welding," Welding Design & Fabrication, Aug. 1978, pp. 70-72.
"Acoustic Sensors Monitor Machine Noise," Machine Design, May 22, 1980, p. 124.

Primary Examiner—C. C. Shaw
Attorney, Agent, or Firm—Donald R. Campbell; James C. Davis, Jr.; Marvin Snyder

[57] ABSTRACT

The thickness of the molten weld nugget is continuously monitored during resistance spot welding, and when proper penetration is achieved the applied current is turned off. An ultrasonic transducer housed in the water cooled lower welding electrode transmits ultrasonic pulses into the workpiece and receives waves reflected at each solid/solid and liquid/solid interface. The position of the latter is tracked by pulse time discrimination of reflected signals; weld nugget penetration is computed using a ratio of times or a pulse time difference.

9 Claims, 13 Drawing Figures

ACOUSTIC WAVE SPOT WELDER ADAPTIVE CONTROL

BACKGROUND OF THE INVENTION

This invention relates to a system and method of determining and controlling weld nugget penetration during resistance spot welding using an acoustic technique. Faulty welds due to lack of penetration can be detected and controlled.

Resistance spot welding setup procedures are often based either on using handbook values or trial and error techniques. Once production parameters have been determined, the spot welding machine current, heat and load are set on the machine controls. Test coupons are made periodically during production and destructively inspected to determine weld nugget size, penetration and strength. This procedure is costly and has lead to faulty welds ending up in production, since test coupons are not always representative of production welding conditions.

There are essentially four types of resistance spot welder process controls on the market and these are categorized according to the variable measured in the welding process. They are: (1) thermal expansion; (2) nugget electrical resistance; (3) electric power; and (4) other methods consisting of ultrasonic, acoustic and infrared type sensing devices. Among the latter is a method based on the stress wave energy emission signature which is compared to an acceptable signal to control the resistance welding process. An acoustic control system has been briefly described that stops weld current at the onset to expulsion. Another author describes a technique using ultrasonic signals which are transmitted through the workpiece during the welding process. The method is based on the effect that temperature and molten metal have on wave velocity and wave distortion. Signature analysis and comparison to a reference are then used to track nugget formation.

An object of this invention is to provide an improved adaptive control system and method which will assure high quality resistance spot welds based on sensing an interior variable such as liquid/solid interface formation. Most other techniques currently available try to obtain weld nugget information by measuring external or response variables such as thermal expansion, temperature, etc., or signatures of internal behavior.

SUMMARY OF THE INVENTION

Weld nugget penetration is continuously computed and controlled during a resistance spot welding operation by an improved method based on reflection of acoustic waves at material discontinuity interfaces. An ultrasonic transmitter/receiver element housed in a water cooled welding electrode transmits ultrasonic pulses into the workpiece to be joined. At each solid/solid interface and liquid/solid interface the longitudinal waves are reflected. The position of the liquid/solid interface is tracked by pulse time discrimination of the reflected waves, and when proper penetration is achieved the applied current is turned off.

In the illustrative embodiment, ultrasonic energy is reflected at interfaces between the electrodes and workpieces, initially at the interface between workpieces, and subsequently at the boundary between liquid and solid zones as the weld nugget grows. The reflected signals are conditioned and digitized before input to a microcomputer to produce narrow spikes at the midpoint of the time value. Weld nugget penetration is determined as a ratio of times or from a pulse time difference. One ratio that gives penetration is the time difference between pulses reflected from the top and bottom boundaries of the molten weld nugget, over the time difference between pulses reflected from the top and bottom workpiece interfaces. The first is related to the thickness of the weld nugget, the second to the combined thickness of the workpiece. Typically the welding current is turned off or tapered down at 60-70% penetration. This adaptive control system assures high quality welds and prevents welds with lack of penetration from getting into the production line.

DETAILED DESCRIPTION OF THE INVENTION

Figure 1:
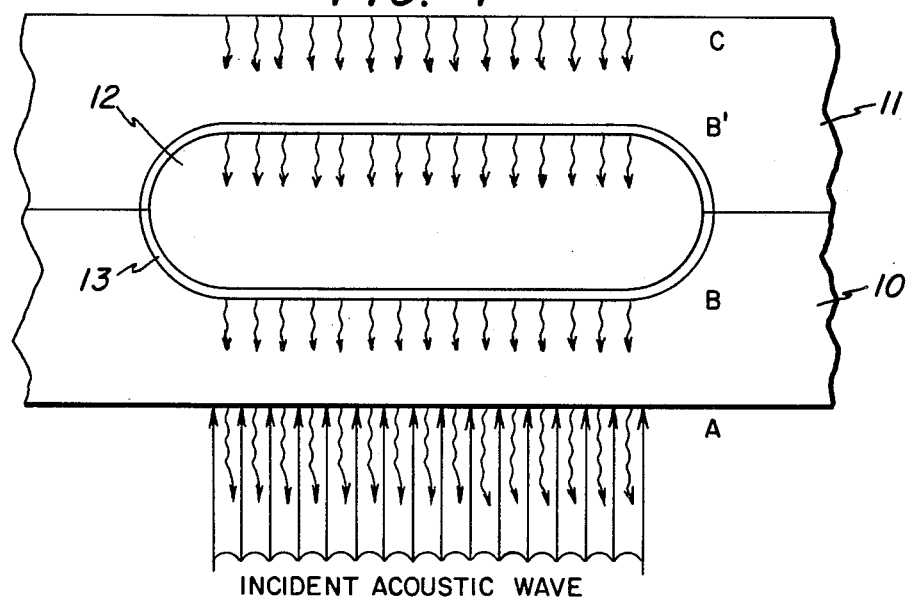
FIG. 1 is a schematic of acoustic wave propagation and reflection by workpiece and weld nugget interfaces.

This invention is based on the reflection laws of acoustic waves which propogate through a continuum. FIG. 1 shows a schematic of the incident acoustic waves and the reflected waves at interfaces A, B, B' and C. Workpieces 10 and 11, typically thin metal sheets, are held between welding electrodes and welded by passage of current which generates heat and forms a pancake-shaped molten weld nugget 12. The liquid and solid zones have completely different acoustic properties, and there is a thin, mushy zone or boundary layer 13 between the liquidus and solidus that causes a distorted signal. At each solid/solid or liquid/solid interface, a wave reflection will occur. Ultrasonic energy is both transmitted and reflected at the electrode/workpiece interface A, and the reflected wave propogates in the direction towards the source. Similarly, at liquid/solid interfaces B and B' and at workpiece/electrode interface C energy is both transmitted and reflected. These reflection waves can be used to measure the thickness of the weld nugget, usually described as penetration. The longitudinal pulse is the acoustic excitation ideally suited for the resistance spot welding process which produces a pancake-shaped molten region. This geometry with essentially two planar surfaces is ideal for the reflection of longitudinal waves with minimum attenuation.

Figure 2A:
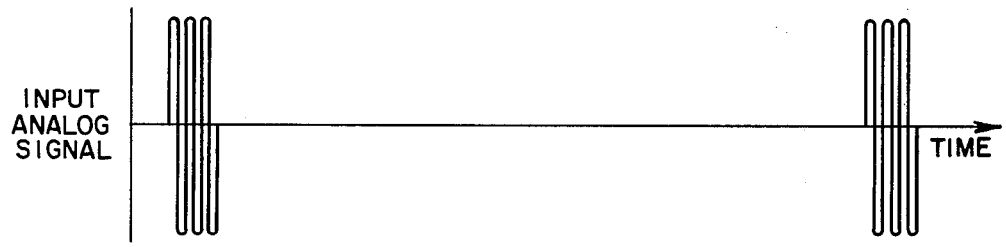
FIGS. 2a-2c are waveform diagrams of the input acoustic pulses, reflected analog signals, and the digitized return signals.
Figure 2B:
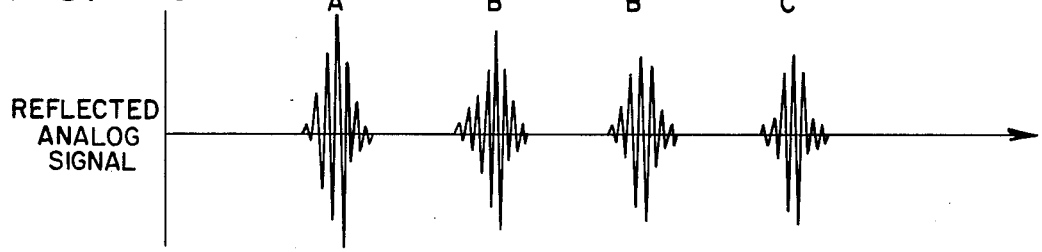
Figure 2C:
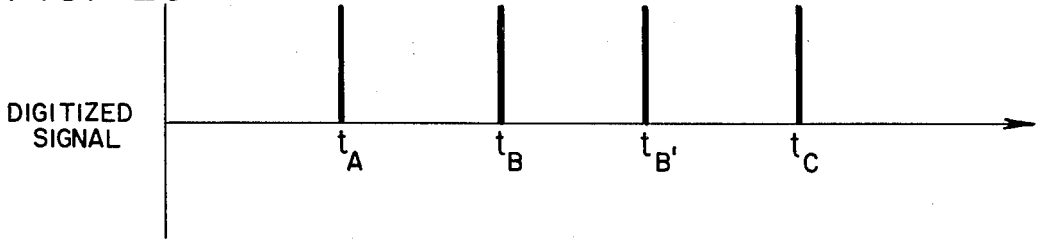
Figure 3A:
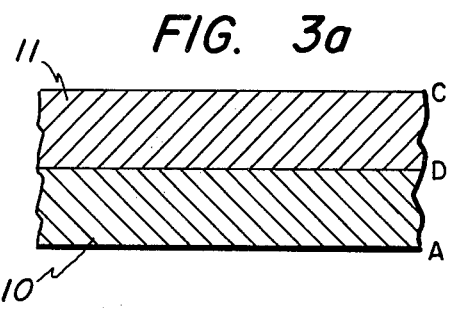
FIGS. 3a, 4a, 5a, and 6a depict workpieces being spot welded.
Figure 3B:
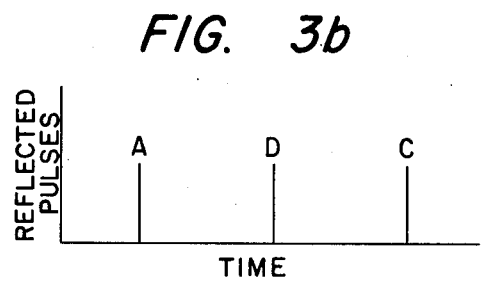
FIGS. 3b, 4b, 5b, and 6b are simplified presentations of the respective reflected pulse trains.
Figure 4A:
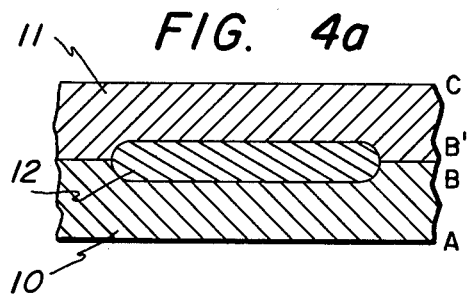
Figure 4B:
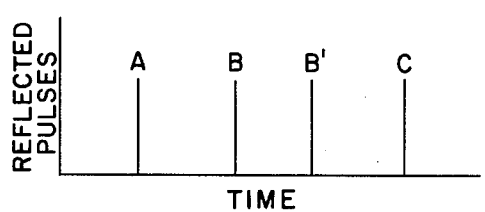
Figure 5A:
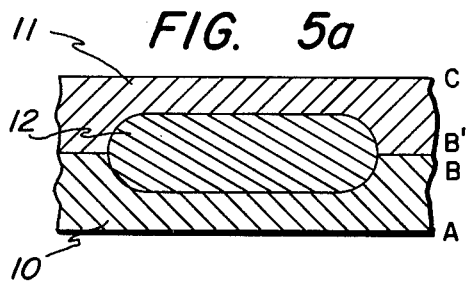
Figure 5B:
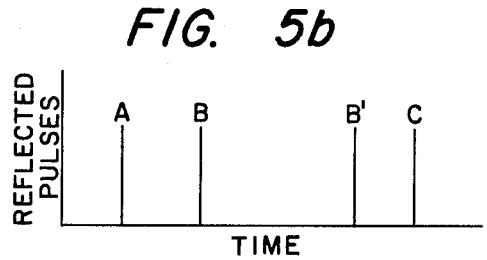

FIGS. 2a-2c are waveform diagrams of the signals and pulse train. The input analog signal, transmitted into the workpiece from an ultrasonic transducer in the lower electrode, is seen in FIG. 2a. The period of these high frequency ultrasonic pulses is sufficiently long that all of the reflected signals are received before the next pulse is launched. For thin materials the pulse frequency is less than 10 megahertz. The reflected analog signals from the four interfaces, FIG. 2b, have a relatively long time duration. These return signals are fed into the adaptive control system where the signal is conditioned and digitized. The signal processing may include filtering out the high frequency components and getting the mid-point value of time. The digitized signal, FIG. 2c, consists of narrow pulses or spikes with equal amplitude at more precisely defined times $t_A$–$t_C$, whereas the amplitude of the analog signals progressively decreases, being smallest for the interface most distant from the transducer.

This invention is based on pulse time discrimination and not waveform analysis, signature analysis, signal shape, amplitude or return pulse time. It is rather based on a ratio of times, or on the discrimination of pulse time differences between waves reflected from liquid/solid and workpiece interfaces. The method of controlling weld nugget penetration during resistance spot welding comprises continuously transmitting acoustic pulses into the workpieces, receiving waves reflected from the interfaces, and tracking the position of the liquid/solid interface by discrimination of reflected signals in the time domain. When proper penetration has been received, the applied current is turned off. A unique feature is that faulty welds due to lack of penetration can be detected and controlled.

FIGS. 3a–5a show two workpieces of equal thickness at different stages of the welding cycle, and in FIGS. 3b–5b are digitized reflected pulse trains, represented as a series of lines. Initially there are reflections from the near and far electrode/workpiece interfaces A and C and from the interface D between the two workpieces. As the weld nugget grows and its thickness increases, there are reflections from liquid/solid interfaces B and B', at the bottom and top boundaries of the molten weld nugget. The positions of reflected pulses B and B' change and the time difference between them increases. Thus, the thickness of the liquid zone is continuously monitored as the welding proceeds. It is observed that the relative positions in time of reflected pulses A and C and the time difference between them remains the same.

Figure 6A:
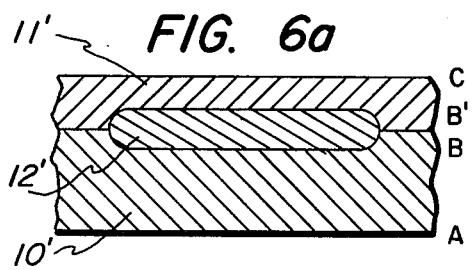
Figure 6B:
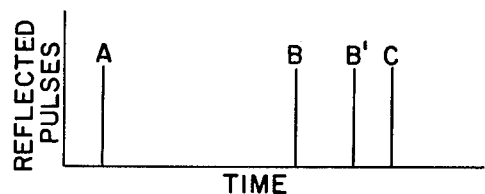

A feature of this method of determining and controlling weld nugget penetration and the adaptive controller for its implementation is that it is valid for welding workpieces of different thicknesses. FIG. 6a has a workpiece 10' that is much thinner than the other workpiece 11' and the molten weld nugget 12' at the faying surface is close to the top of the combined workpiece. Reflected pulses B and B' in FIG. 6b are much closer to interface C than in the figures above. Penetration is calculated in the same way as for equal thickness workpieces.

One time ratio that yields weld nugget penetration is the time difference between signals reflected from the top and bottom interfaces of the molten weld nugget over the time difference between reflections from the top and bottom of the workpiece.

$$\text{Weld Nugget Penetration} = \frac{t_B - t_{B'}}{t_C - t_A} \quad (1)$$

The time difference in the numerator is related to the thickness of the weld nugget and that in the denominator to the combined thickness of the material.

Another ratio of times that may be used is the time difference between reflections at one liquid/solid interface and electrode/workpiece interface, say B and A, over the time difference between reflections at interfaces D and A.

$$\text{Weld Nugget Penetration} = 1 - \frac{t_B - t_A}{t_D - t_A} \quad (2)$$

Another approach is to continuously compute the velocity of ultrasound in the workpiece, measure their combined thickness and from these calculate percent penetration.

Figure 7:
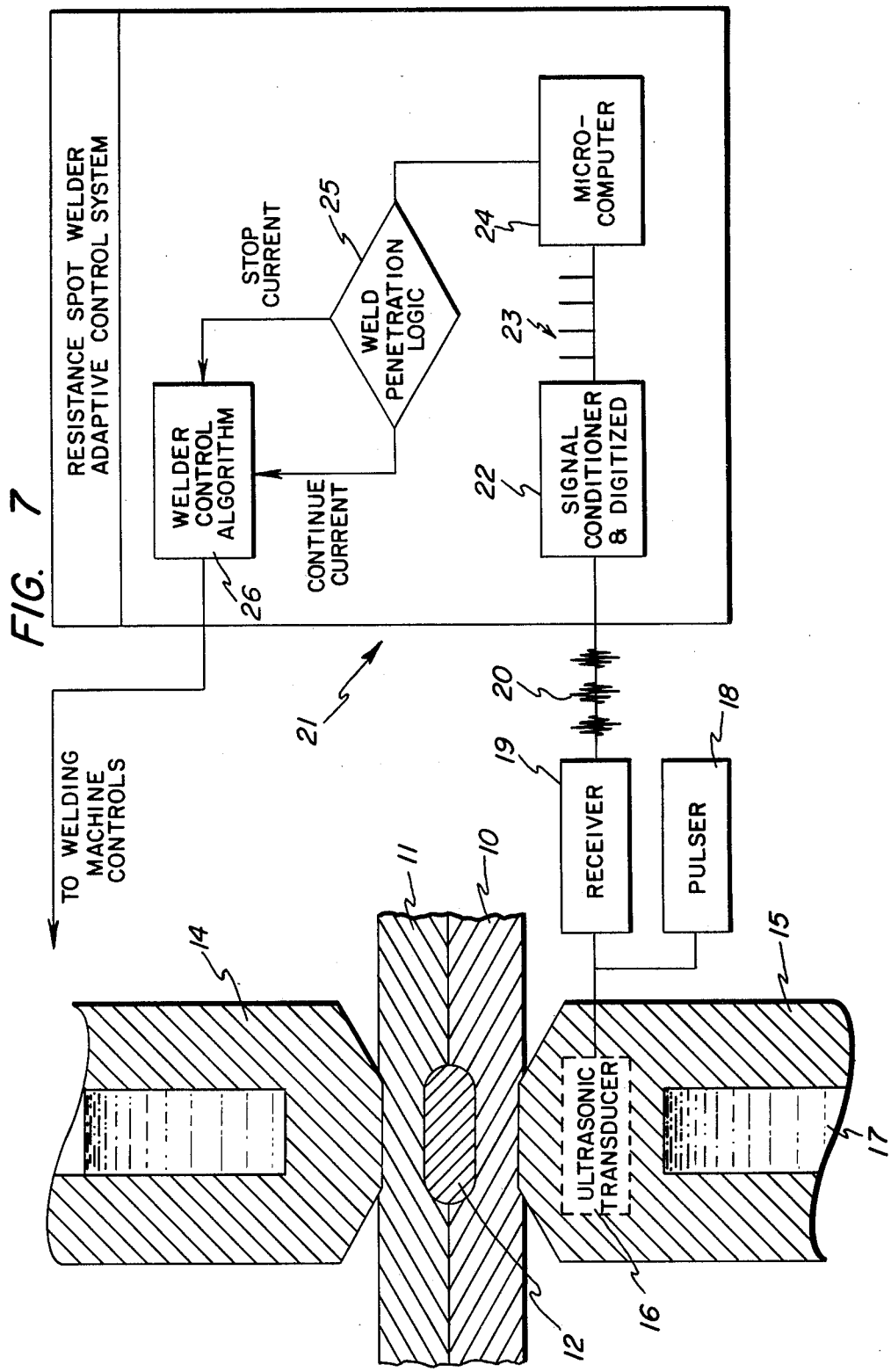
FIG. 7 is a vertical cross section through the water cooled welding electrodes positioned to weld a workpiece and a diagram of the adaptive control system.

FIG. 7 has a simplified schematic of a resistance spot welder adaptive control system for a conventional welding machine; only part of the truncated electrodes 14 and 15 positioned to make a spot weld on thin metal workpieces are illustrated. The lower water cooled copper electrode 15 houses the ultrasonic transmitting and receiving transducer 16, mounted in a cavity between the end of the electrode and the central cooling channel 17. It is essential that the transducer, preferably one having a piezoelectric element, not be subjected to elevated temperatures. The electronics, including a pulser 18 to generate excitation voltages and a receiver 19 to amplify the signals, are outside the electrode and may be in the controller box. The reflected analog electrical signals 20 are fed into the adaptive control system 21 and are sent to the signal conditioning and digitizing circuitry 22. The digitized signal 23 consisting of a set of narrow spikes is presented to a microcomputer 24. The time differences between reflected signals are derived and penetration is computed.

After loading the workpiece into the welding machine, lowering the upper electrode to apply compressive force, and turning on the welding current, ultrasonic pulses are transmitted upward through the workpiece during the welding process. Sets of reflected signals, one set per transmitted pulse, are continuously fed to the microcomputer and penetration is calculated, for instance by equation (1). Proper penetration is achieved when the value of this time ratio is approximately 0.6 to 0.7. The changing penetration value is presented to weld penetration logic 25 which issues of continue current command until the required penetration is achieved and then sends out a stop current command. Lack of penetration and a stuck weld, or a welding machine malfunction, are indicated by failure to reach the required penetration within a preset time limit. Welder control algorithm 26 tapers down the high amperage current after receiving a stop current command and then orders the machine to go into the hold cycle. It may embody a rate of cooling control to temper the workpiece and reduce thermal stresses across the weld zone which would be produced from normal more rapid cooling. Transmission of ultrasonic pulses into the workpiece is stopped before the end of the complete welding cycle.

An improved method of measuring and controlling weld nugget penetration and a resistance spot welder adaptive control system to practice the method is needed to assure high quality welds and prevent welds with lack of penetration from getting into the field. This acoustic technique, based on wave reflection at interfaces between materials, accurately and continuously tracks the melt front location by discrimination of reflected pulses in the time domain.

While the invention has been particularly shown and described with reference to preferred embodiments thereof, it will be understood by those skilled in the art that various changes in form and details may be made therein without departing from the spirit and scope of the invention.

The invention claimed is:

1. A method of controlling weld nugget penetration during resistance spot welding comprising:
   transmitting longitudinal acoustic pulses into a workpiece held between electrodes and welded by passage of current which generates heat and forms a molten weld nugget;
   receiving waves reflected from solid/solid and liquid/solid workpiece interfaces;
   tracking the position of at least one liquid/solid interface as the weld nugget grows by pulse time discrimination of reflected waves; and
   turning off the current when proper weld penetration is achieved.

2. The method of claim 1 wherein weld nugget penetration is determined by a ratio of times at which waves are reflected from said interfaces.

3. The method of claim 1 wherein weld nugget penetration is based on discrimination of pulse time differences between waves reflected from said interfaces.

4. A method of adaptively controlling a resistance spot welding process by an ultrasonic technique comprising:
   holding workpieces between upper and lower electrodes and passing current therethrough to generate heat and form a molten weld nugget;
   transmitting ultrasonic pulses into said workpieces from a transmitter/receiver transducer element housed in said lower electrode;
   receiving signals reflected at interfaces between said electrodes and workpieces, initially at the interface between workpieces, and subsequently as said weld nugget grows at the boundaries between liquid and solid zones;
   conditioning and digitizing said reflected signals;
   continuously computing weld nugget penetration by discrimination of said reflected signals in the time domain; and
   turning off the current when a required penetration is achieved.

5. The method of claim 4 wherein penetration is a ratio of time differences between reflected signals related to the thickness of said weld nugget and to the thickness of said workpieces.

6. The method of claim 5 wherein said time differences are between reflections at both liquid/solid interfaces and between reflections at both electrode/workpiece interfaces.

7. The method of claim 4 wherein the conditioning and digitizing step comprises producing a narrow pulse approximately at the midpoint of the time value of each reflected signal.

8. The method of claim 7 wherein said workpieces have unequal thicknesses.

9. An improved adaptive control system for a resistance spot welding machine having upper and lower liquid cooled electrodes to hold a workpiece which is welded by passage of current, comprising:
   ultrasonic transducer means housed in said lower electrode for transmitting pulses of ultrasound into said workpiece and receiving energy reflected from electrode/workpiece interfaces and boundaries between liquid and solid zones as a molten weld nugget forms and grows, and means for applying excitation voltages to said transducer means and amplifying received signals; and
   an adaptive control system having means for conditioning and digitizing said reflected signals to provide sets of narrow digitized pulses approximately at the midpoints of said reflected signals, means for continuously computing weld nugget penetration by discrimination of said digitized pulses in the time domain and taking pulse time differences, and means for sending commands to the machine controls to taper down and stop the current when proper penetration is achieved.

* * * * *